United States Patent [19]

Dotson, Jr. et al.

[11] 4,322,565

[45] Mar. 30, 1982

[54] PROCESS FOR PURIFYING ETHERS

[75] Inventors: Anderson O. Dotson, Jr.; Francis T. Wadsworth, both of Monroe, La.

[73] Assignee: Columbian Chemicals Company, Tulsa, Okla.

[21] Appl. No.: 224,420

[22] Filed: Jan. 12, 1981

Related U.S. Application Data

[63] Continuation-in-part of Ser. No. 69,210, Aug. 23, 1979.

[51] Int. Cl.$^3$ ............................................. C07C 41/06
[52] U.S. Cl. .................................... 568/697; 568/699; 568/923
[58] Field of Search ............... 568/697, 699, 923, 918

[56] References Cited

U.S. PATENT DOCUMENTS

| | | | |
|---|---|---|---|
| 1,442,520 | 1/1923 | Buc | 568/699 |
| 2,179,991 | 11/1939 | Bright et al. | 568/923 |
| 3,940,450 | 2/1976 | Lee | 568/699 |

FOREIGN PATENT DOCUMENTS

7807035  1/1979  Netherlands ........................ 568/697

OTHER PUBLICATIONS

Monick, "Alcohols", 1968, p. 561.

*Primary Examiner*—Joseph E. Evans
*Attorney, Agent, or Firm*—Patricia J. Hogan

[57] ABSTRACT

An alkyl t-alkyl ether corresponding to the formula R—O—R', wherein R is a methyl or ethyl group and R' is a t-butyl or t-amyl group, is separated from the alkanol in a reactor effluent comprising a mixture of the ether, unreacted $C_1$–$C_2$ alkanol, and unreacted hydrocarbon by (1) alternately passing effluent from the reactor through first and second absorption vessels containing fixed beds of solid calcium chloride to complex the unreacted alkanol with the calcium chloride while the ether and unreacted hydrocarbon pass through the vessel, (2) while one absorption vessel is being used to complex unreacted alkanol, regenerating the other absorption vessel by passing a liquid $C_4$ or $C_5$ hydrocarbon feed comprising an isoolefin therethrough at a temperature of about 80°–120° C. to desorb the alkanol and provide a desorption effluent of liquid $C_4$ or $C_5$ hydrocarbon feed and alkanol, and (3) feeding the desorption effluent to the reactor.

4 Claims, No Drawings

4,322,565

PROCESS FOR PURIFYING ETHERS

CROSS-REFERENCE TO RELATED APPLICATION

This application is a continuation-in-part of copending application Ser. No. 69,210, filed Aug. 23, 1979.

BACKGROUND OF THE INVENTION

1. Field of the Invention

This invention relates to alkyl t-alkyl ethers and more particularly relates to a process for separating such ethers from alkanols.

2. Description of the Prior Art

As shown in Netherlands published application No. 7,807,035 (Snam Progetti); U.S. Pat. Nos. 3,940,450 (Lee) and 4,148,695 (Lee et al.); John C. Davis et al., "MTBE bandwagon," CHEMICAL ENGINEERING, May 21, 1979, pp. 91-93; and Stephen C. Stinson, "New plants, processes set for octane booster," CHEMICAL & ENGINEERING NEWS, June 25, 1979, pp. 35 and 36, it is known that alkyl t-alkyl ethers can be prepared by reacting an isoolefin with an alkanol in the presence of an ion exchange resin. Such reactions have general interest, although the greatest current interest is in the reaction of isobutylene with methanol to form methyl t-butyl ether. Methyl t-butyl ether has utility as an additive for improving the octane rating of gasoline.

In the reactions of isoolefins with alkanols, it is preferred to use an excess of alkanol in order to minimize the formation of by-products. However, the use of an excess of alkanol results in contaminating the ether product with a difficultly removable impurity. The alkanol forms an azeotrope with the ether and therefore cannot be separated therefrom by simple atmospheric distillation.

It is frequently desirable to separate the alkanol from the ether. It is also desirable to separate the alkanol from any unreacted hydrocarbons in the crude reaction product, since alkanols are poisons for alkylation catalysts and, if not removed, would make the unreacted hydrocarbons unsuitable for use in alkylation units. Thus, since atmospheric distillation canot be used, it is conventional to remove the alkanol by pressure distillation. This method of removing the alkanol is costly in terms of energy requirements and capital investment.

An economical and efficient process for separating alkanols from alkyl t-alkyl ethers and unreacted hydrocarbons is disclosed in copending application Ser. No. 69,210, filed Aug. 23, 1979, in the names of Anderson O. Dotson, Jr., and Francis T. Wadsworth. In the process of that application, solid or aqueous calcium chloride is intimately admixed with an ether-alkanol mixture to form a calcium chloride-alkanol complex which is easily separable from the ether. The application teaches that the aqueous solutions are generally more efficient than solid calcium chloride and are particularly suitable for use in processes wherein the alkanol is to be recovered and recycled to a reactor.

Copending application Ser. No. 142,272, filed Apr. 21, 1980, in the names of Anderson O. Dotson, Jr., and Francis T. Wadsworth, now U.S. Pat. No. 4,262,149, teaches an improvement over the preferred process of Ser. No. 69,210, wherein an aqueous calcium chloride-alkanol complex is contacted with a $C_4$ or $C_5$ hydrocarbon feed comprising an isoolefin at a temperature of about 80°-120° C. and a pressure of about 20-180 psig to separate the components of the complex and permit their reuse.

Although the processes of the aforementioned copending applications are economical and efficient, they have one disadvantage. The use of aqueous calcium chloride to complex the alkanol creates corrosion problems.

SUMMARY OF THE INVENTION

An object of this invention is to provide an economical process for separating $C_1$-$C_2$ alkanols from ethers corresponding to the formula R—O—R', wherein R is methyl or ethyl and R' is a t-butyl or t-amyl group.

Another object is to provide such a process which permits recovery and reuse of the alkanols.

A further object is to provide such a process which does not present corrosion problems.

These and other objects are attained by (1) taking the ether/unreacted alkanol/unreacted hydrocarbon reactor effluent obtained by reacting an excess of a $C_1$-$C_2$ alkanol with an isoolefin containing 4 or 5 carbon atoms, (2) alternately passing this effluent through first and second absorption vessels, each containing a fixed bed of solid calcium chloride, to complex the unreacted alkanol with the calcium chloride while the ether and unreacted hydrocarbon pass through the vessel, (3) while one absorption vessel is being used to complex unreacted alkanol, regenerating the other absorption vessel by passing a liquid $C_4$ or $C_5$ hydrocarbon feed comprising an isoolefin therethrough at a temperature of about 80°-120° C. to desorb the alkanol and provide a desorption effluent of liquid $C_4$ or $C_5$ hydrocarbon feed and alkanol, and (4) feeding the desorption effluent to the reactor.

DESCRIPTION OF THE PREFERRED EMBODIMENTS

The ether/unreacted alkanol/unreacted hydrocarbon reactor effluent that is treated in accordance with the invention is the crude reaction product resulting from the reaction of an excess of methanol or ethanol with isobutylene or isoamylene to form an alkyl t-alkyl ether corresponding to the formula R—O—R', wherein R is a methyl or ethyl group and R' is a t-butyl or t-amyl group. Such reactions are well known and include processes wherein the alkanol is reacted with pure isoolefin and processes wherein the alkanol is reacted with a steam-cracker or catalytic-cracker $C_4$ or $C_5$ hydrocarbon stream containing the isoolefin and other hydrocarbons primarily having the same number of carbon atoms. A typical process utilizes a $C_4$ hydrocarbon stream containing 25-55% by weight of isobutylene, a methanol/isobutylene mol ratio of 1.7, an ion exchange resin as a catalyst, a reaction temperature of about 90°-100° C., and a pressure of about 280 psig, although other reactants and other conditions are also utilizable when desired.

As is also well known, the crude reaction products resulting from such processes are generally mixtures of the desired ether, unreacted alkanol, unreacted hydrocarbon, and small amounts of by-products, although by-product formation is minimized by the use of an excess of the alkanol. For example, in the typical process mentioned above, the crude reaction product typically contains methyl t-butyl ether, methanol, isobutylene, n-butane, isobutane, cis-butene-2, trans-butene-2, butene-1, and small amounts of t-butyl alcohol and diisobutylene. On the other hand, when pure isoolefin is used as a starting material, isoolefin is the only unreacted hydrocarbon in the crude reaction product.

In the practice of the invention, the unreacted alkanol in the crude reaction product is separated from the ether and unreacted hydrocarbon by alternately passing the reactor effluent through first and second absorption vessels, each containing a fixed bed of solid calcium chloride, to complex the unreacted alkanol with the calcium chloride while the ether and unreacted hydrocarbon pass through the vessel. Preferably the reactor effluent is passed upwardly through the absorption vessels to prevent channeling. The ether and unreacted hydrocarbon may be collected at the exits of the absorption vessels and separated from one another by conventional means, e.g., simple atmospheric distillation.

The absorption vessels may be any vessels suitable for holding solid calcium chloride which is to be regenerated by a liquid $C_4$ or $C_5$ hydrocarbon feed, and they are generally pressure vessels suitable for operating at the pressures that will be required to keep the hydrocarbon feed in the liquid state, e.g., about 200–400 psig. The reactor effluent may be fed thereto by conventional means, suitably with the use of a valving arrangement that permits ready transfer of the flow of the effluent from one absorption vessel to the other.

The flow of the reactor effluent may be transferred from one absorption vessel to the other at any time that permits substantially complete separation of the unreacted alkanol from the ether and unreacted hydrocarbon. However, most efficiently, each absorption vessel is used to absorb unreacted alkanol from the reactor effluent until the absorptive capacity of its calcium chloride is substantially exhausted before the flow is transferred to the other vessel. The absorptive capacity of a given bed of solid calcium chloride can be determined by a trial run or can be theoretically determined on the basis that the bed should contain at least 0.25 mol of calcium chloride per mol of alkanol to be absorbed by the bed before the flow of reactor effluent is to be transferred to the other absorption vessel.

As mentioned above, each absorption vessel is regenerated while the other is being used to complex unreacted alkanol. This regeneration is accomplished by passing a liquid $C_4$ or $C_5$ hydrocarbon feed through the vessel at a temperature of about 80°–120° C., conveniently in an upward direction. The feed is generally heated to 80°–120° C. before being passed through the vessel. While the vessel is being regenerated, it is maintained under pressure, e.g., a pressure of about 200–400 psig, to keep the hydrocarbon feed in the liquid state.

The hydrocarbon feed used to regenerate the absorption vessels may be any $C_4$ or $C_5$ hydrocarbon feed comprising an isoolefin. Thus, it may be pure, or at least substantially pure, isobutylene or isoamylene or a $C_4$ or $C_5$ hydrocarbon stream, e.g., a steam-cracker or catalytic-cracker stream, containing the isoolefin and other hydrocarbons primarily having the same number of carbon atoms. In a preferred embodiment of the invention, it is a $C_4$ hydrocarbon stream containing isobutylene.

The amount of hydrocarbon feed employed to regenerate the absorption vessels is not critical, since the calcium chloride in the vessels does not have to be completely free of complexed alkanol to make it utilizable for complexing more alkanol. However, it is generally preferred to desorb at least most of the alkanol that has been complexed with the calcium chloride. Excellent results may be achieved by using at least about 1.3 parts by weight of hydrocarbon feed per part of complexed alkanol. Frequently the total weight of hydrocarbon feed employed is in the range of about 1.3–3 times the weight of complexed alkanol.

The passage of the hydrocarbon feed through the absorption vessel results in desorption of the complexed alkanol and the provision of a desorption effluent of liquid $C_4$ or $C_5$ hydrocarbon feed and alkanol. The desorption effluent is fed to the reactor, where it may be combined with any necessary make-up alkanol and isoolefin; and the absorption vessel is used again to absorb unreacted alkanol from reactor effluent.

The invention is particularly advantageous in that it provides an economical method of separating alkanols from alkyl t-alkyl ethers in such a way as to permit recovery and reuse of the alkanols, in that it requires no stirring or the use of solvents other than feedstock for the reactor, and in that it presents no corrosion problems.

The following example is given to illustrate the invention and is not intended as a limitation thereof. Unless otherwise specified, quantities mentioned in the example are quantities by weight.

EXAMPLE

Charge a mixture of 221 parts of methanol and 450 parts of a $C_4$ hydrocarbon stream containing 50.8% isobutylene to a tubular reactor packed with an acidic ion exchange resin. React the ingredients at 100° C. to form a reaction mixture comprising methyl t-butyl ether, excess methanol, and unreacted hydrocarbons. Withdraw this reaction mixture from the bottom of the reactor through a conduit leading to two valved pressure vessels, each of which is packed with 40 parts of solid calcium chloride and each of which is provided with a collection vessel at its exit.

While the valve to the second pressure vessel is closed, feed the reactor effluent upwardly through the first pressure vessel until the amount of methanol fed to the vessel approaches the amount theoretically capable of exhausting the ability of the calcium chloride in the vessel to complex it, while withdrawing methanol-free methyl t-butyl ether and unreacted hydrocarbons in the collection vessel. Then close the valve to the first pressure vessel, open the valve to the second pressure vessel, and feed reactor effluent upwardly through the second pressure vessel until the amount of methanol fed to the vessel approaches the amount theoretically capable of exhausting the ability of the calcium chloride in the vessel to complex it, while withdrawing methanol-free methyl t-butyl ether and unreacted hydrocarbons in the collection vessel.

While the reactor effluent is being fed through the second pressure vessel, pump 60 parts of a $C_4$ hydrocarbon stream containing 50.8% isobutylene upwardly through the first pressure vessel at a temperature of 100° C. and a pressure of 300 psig to desorb the complexed methanol and form a desorption effluent of the hydrocarbon stream and eluted methanol. Feed the desorption effluent to the reactor and combine it with sufficient make-up methanol and hydrocarbon stream to form a reaction mixture having the same composition as the original reaction mixture. Then subject the reaction mixture to reaction conditions and withdraw the crude reaction product as before.

When absorption of methanol in the second pressure vessel has been carried to the desired degree, close the valve to that vessel, open the valve to the first pressure vessel, and continue to alternate using the vessels for absorption of excess methanol while regenerating the other vessel.

Separate the methyl t-butyl ether and unreacted hydrocarbons in the collection vessels by atmospheric distillation. The process leads to the isolation of methyl t-butyl ether and $C_4$ hydrocarbons that are substantially free of methanol.

We claim:

1. In a process for preparing an ether by reacting an excess of a $C_1$-$C_2$ alkanol with an isoolefin containing 4 or 5 carbon atoms to form a reactor effluent comprising a mixture of (1) an ether corresponding to the formula R—O—R', wherein R is a methyl or ethyl group and R' is a t-butyl or t-amyl group, (2) unreacted alkanol, and (3) unreacted hydrocarbon, the improvement which comprises:

(A) alternately passing effluent from the reactor through first and second absorption vessels, each containing a fixed bed of solid calcium chloride, to complex the unreacted alkanol with the calcium chloride while the ether and unreacted hydrocarbon pass through the vessel, (B) while one absorption vessel is being used to complex unreacted alkanol, regenerating the other absorption vessel by passing a liquid $C_4$ or $C_5$ hydrocarbon feed comprising an isoolefin therethrough at a temperature of about 80°–120° C. to desorb the alkanol and provide a desorption effluent of liquid $C_4$ or $C_5$ hydrocarbon feed and alkanol, and (C) feeding the desorption effluent to the reactor.

2. The process of claim 1 wherein (1) the reactor effluent is the crude reaction product obtained by reacting an excess of methanol with a $C_4$ hydrocarbon stream containing isobutylene and (2) the hydrocarbon feed used to regenerate the absorption vessels is a $C_4$ hydrocarbon stream containing isobutylene.

3. The process of claim 1 wherein the weight of hydrocarbon feed added to the absorption vessel is at least about 1.3 times the weight of alkanol complexed with the calcium chloride.

4. The process of claim 1 wherein each absorption vessel is used to absorb unreacted alkanol from the reactor effluent until the absorptive capacity of its calcium chloride is substantially exhausted.

* * * * *